United States Patent
Schertler et al.

(10) Patent No.: US 10,899,805 B2
(45) Date of Patent: Jan. 26, 2021

(54) HUMAN G PROTEIN ALPHA SUBUNIT GAIL WITH AT LEAST ONE MUTATED AMINO ACID RESIDUE

(71) Applicant: PAUL SCHERRER INSTITUT, Villigen Psi (CH)

(72) Inventors: Gebhard Schertler, Hertenstein (CH); Dawei Sun, Newark, CA (US); Dmitry Veprintsev, Baden (CH)

(73) Assignee: Paul Scherrer Institut, Villigen (CH)

( * ) Notice: Subject to any disclaimer, the term of this patent is extended or adjusted under 35 U.S.C. 154(b) by 0 days.

(21) Appl. No.: 15/516,458

(22) PCT Filed: Sep. 2, 2015

(86) PCT No.: PCT/EP2015/070067
§ 371 (c)(1),
(2) Date: Apr. 3, 2017

(87) PCT Pub. No.: WO2016/050441
PCT Pub. Date: Apr. 7, 2016

(65) Prior Publication Data
US 2017/0298111 A1    Oct. 19, 2017

(30) Foreign Application Priority Data
Oct. 2, 2014 (EP) .................................. 14187459

(51) Int. Cl.
| | |
|---|---|
| *C07K 14/47* | (2006.01) |
| *C07K 1/00* | (2006.01) |
| *C07K 14/435* | (2006.01) |
| *C07K 14/00* | (2006.01) |
| *C12N 9/00* | (2006.01) |

(52) U.S. Cl.
CPC ............ *C07K 14/4722* (2013.01); *C07K 1/00* (2013.01); *C07K 14/435* (2013.01); *C07K 14/00* (2013.01); *C12N 9/00* (2013.01); *G01N 2333/726* (2013.01); *G01N 2500/00* (2013.01)

(58) Field of Classification Search
None
See application file for complete search history.

(56) References Cited

U.S. PATENT DOCUMENTS

| | | |
|---|---|---|
| 6,004,808 A | 12/1999 | Negulescu et al. |
| 2005/0108791 A1 | 5/2005 | Edgerton |
| 2011/0212476 A1 | 9/2011 | Lowery et al. |
| 2017/0051031 A1 | 2/2017 | Maletinska et al. |

FOREIGN PATENT DOCUMENTS

| | | |
|---|---|---|
| CN | 101516907 A | 8/2009 |
| WO | 9748820 A1 | 12/1999 |
| WO | 2015180698 A1 | 12/2015 |

OTHER PUBLICATIONS

Kaya AL et al:"A Conserved Phenylalanine as a Relay between the α5 Helix and the GDP Binding Region of Heterotrimenc Gi Protein α Subunit"; The Journal of Biological Chemistry vol. 289, No. 35, pp. 24475-24487, Aug. 29, 2014.
Donna S. Woulfe, et al., "Structural Basis for the Selectivity of the RGS Protein, GAIP, for Gαi Family Members", "Identification of a Single Amino Acid Determinant for Selective Interaction of Gαi Subunits With GAIP*" 1999, The Journal of Biological Chemistry vol. 274, No. 25, pp. 17718-17724,(Jan. 13, 1999).
Mark A Wall et al., "Structural basis of activity and subunit recognition in G protein hererotrimers", Current Biology Publications ISSN 0969-2126, Structure, 1998, vol. 6, No. 9, pp. 1169-1183, (Sep. 15, 1998).
Tilman Flock et al: "Universal allosteric mechanism for Gα activation by GPCRs", Nature, vol. 524, Aug. 13, 2015 (Aug. 13, 2015), pp. 173-179, XP055371482, GB ; ISSN: 0028-0836, DOI: 10.1038/nature14663.
Rondard P. et al.: "Mutant G protein α subunit activated by Gβγ: A model for receptor activation ?", PNAS vol. 98, No. 11. pp. 6150-6155 (May 22, 2001).
Flock, et al.: "Universal Allosteric Mechanism for Ga Activation by GPCRs", Nature vol. 524, No. 7564, Aug. 13, 2015, Supplemental Material Retrieved from the Internet: https://media-nature-com.libproxy.vassar.edu/original/nature-assets/nature/journal/v524/n7564/extref/nature14663-s1.pdf.
Flock, et al.: "Universal Allosteric Mechanism for Ga Activation by GPCRs", Nature vol. 524, No. 7564, Aug. 13, 2015, Supplementary Tables 1, 2 and 3 and Supplementary Data Retrieved from the Internet: https://www-nature-com.ibproxy.vassar.edu/articles/nature14663.
Dawei, Sun, et al.; "Probing G[alpha]i 1 protein activation at single-amino acid resolution;" Nature Structural and Molecular Biology, vol. 22, No. 9; pp: 686-694; XP055231298; ISSN: 1545-9993; DOI: 10.1038/nsmb.3070.

*Primary Examiner* — Michael D Pak
(74) *Attorney, Agent, or Firm* — Laurence Greenberg Werner Stemer; Ralph Locher (57) ABSTRACT

The present application discloses in detail mutant ligands of the human G protein alpha-subunit -Gαi1-, wherein at least one amino acid residue has been replaced with alanine if the at least one amino acid residue is a non-alanine residue, or at least one amino acid residue has been replace with glycine if the at least one amino acid residue is alanine and wherein the at least one amino acid residue is comprised in a first group containing of the amino acid residues with position R32A, K54A, I55A, I56A, H57A, R176A, E245A, Y296A, T327A, N331A, V332A and D350A or is comprised in a second group containing G42A, A59G, T177A, D200A, A226G, E297A, A300G and F334A or is comprised in a third group containing V50A, A59G, R178A 30 and K180A.

2 Claims, 9 Drawing Sheets
Specification includes a Sequence Listing.

Probing Gα$_z$ Protien Activation at Single Amino Acid Resolution

Legends for Tables 1 to 3: Summary of Alanine Scanning Mutagenesis of Gα$_z$

| | | |
|---|---|---|
| alanine mutants: | Ala | |
| wild-type: | WT | |
| Melting temperature: | T$_m$ | |
| Standard deviation: | STD | |
| Common G protein numbering system: | CGN (see the accompanying manuscript by Flock et al) | |
| Column A: | Domain | Gα domain (G-GTPase domain, H-helical domain) |
| Column B: | Gα SSE | Standardized Gα consensus secondary structure element (SSE) name. |
| Column C: | Alternative Name | Alternative name for the SSE used in literature. |
| Column D: | CGN_pos | Position in human reference alignment. |
| Column E: | CGN | CGN identifier for position. |
| Column F: | human Gαz1 sequence | |
| Column G: | Residue number | Residue number of human Gα$_z$ Sequence. |
| Column H: | Alanine mutants | Alanine mutants of human Gα$_z$. |
| Column I: | T$_m$, °C (GDP) | T$_m$ of Gα$_z$ alanine mutants (w/ 1mM GDP) |
| Column J: | STD | STD of T$_m$ (GDP) |
| Column K: | ΔT$_m$, °C (GDP) | T$_m$ of Gα$_z$(Ala) (w/ 1mM GDP) - T$_m$ of Gα$_z$(WT) (w/ 1mM GDP) |
| Column L: | STD | STD of ΔT$_m$ (GDP) |
| Column M: | T$_m$, °C (GTPγS) | T$_m$ of Gα$_z$ alanine mutants (w/ 1mM GTPγS) |
| Column N: | STD | STD of T$_m$ (GTPγS) |
| Column O: | ΔT$_m$, °C (GTPγS) | T$_m$ of Gα$_z$(Ala) (w/ 0.1mM GTPγS) - T$_m$ of Gα$_z$(WT) (w/ 0.1mM GTPγS) |
| Column P: | STD | STD of ΔT$_m$ (GTPγS) |
| Column Q: | complex formation efficiency (%) | complex formation efficiency(R*-G$_z$(Ala)) - complex formation efficiency(R*-G$_z$(WT)) |
| Column R: | complex stability (%) | complex stability(R*-G$_z$(Ala)) - complex stability(R*-G$_z$(WT)) |
| Column S: | Remark | NM: Not measurable |

HUMAN G PROTEIN ALPHA SUBUNIT GAIL WITH AT LEAST ONE MUTATED AMINO ACID RESIDUE

CROSS-REFERENCE TO RELATED PATENT APPLICATIONS

This application is a National Phase filing under 35 U.S.C. § 371 of PCT Patent Application No. PCT/EP2015/070067, filed Sep. 2, 2015, which is based upon and claims the priority of EP Application No. 14187459.4, filed Oct. 2, 2014, each of which is incorporated herein by reference.

SEQUENCE LISTING

The instant application contains a Sequence Listing which has been submitted in ASCII format via EFS-Web and is hereby incorporated by reference in its entirety.

FIELD OF THE INVENTION

The present invention relates to the Human G protein alpha subunit $G\alpha_{i1}$ with at least one mutated amino acid residue, and equivalent amino acid positions in other $G\alpha$ proteins.

BACKGROUND OF THE INVENTION

GPCRs, the largest integral membrane protein family in human genome, perceive a variety of external stimuli and transduce them into intracellular signals by activating heterotrimeric G protein. Heterotrimeric G protein is composed by $G\alpha$, $G\beta$ and $G\gamma$ subunit. The activation of G protein promoted by GPCRs is facilitated by the exchange of GDP to GTP in the $G\alpha$ subunit. The nucleotide exchange leads to the release of the G protein from the receptor and the dissociation of G protein into $G\alpha$ and obligatory $G\beta\gamma$ subunit which further mediate the intracellular signalling by regulating downstream effectors. $G\alpha$ subunit, as one major participant in activation pathway, belongs to the classic Ras protein families, but distinct from other GTP-binding proteins in presence of an alpha-helical domain (HD domain), except the Ras-like domain (GTPase domain).

In the recent years, the significant progress has been achieved in understanding GPCR-mediated G protein activation by the emergence of crystal structure of β2 adrenergic receptor ($\beta_2$AR)-Gs complex ($\beta_2$AR/Gs). It not only demonstrates c-terminal of α5-helix as the key interaction site for receptor, but also verifies the rotation of α5-helix and displacement of HD domain. However, the static view of complex structure and past studies focusing in particular residues still cannot provide the coherent picture of how GPCRs propagate the signal through c-terminal of $G\alpha$ to cause allosteric activation of G protein and release GDP.

SUMMARY OF THE INVENTION

It is therefore the objective of the present invention to provide the human $G\alpha$ protein alpha subunit $G\alpha_{i1}$ with at least one mutated amino acid residue wherein this mutation shall have a higher binding characteristic to the GPCR as compared to the wild type. Alternatively, it could also have higher stability in the absence of a GPCR.

This objective is achieved according to the present invention by a mutant ligand of the human G protein alpha-subunit -$G\alpha_{i1}$-, wherein at least one amino acid residue has been replaced with alanine if the at least one amino acid residue is a non-alanine residue, and wherein the at least one amino acid residue is comprised in a first group containing of the amino acid residues with position R32A, K54A, I55A, I56A, H57A, R176A, E245A, Y296A, T327A, N331A, V332A and D350A or is comprised in a second group containing G42A, A59G, T177A, D200A, A226G, E297A, A300G and F334A or is comprised in a third group containing V50A, A59G, R178A and K180A.

Figure 9:
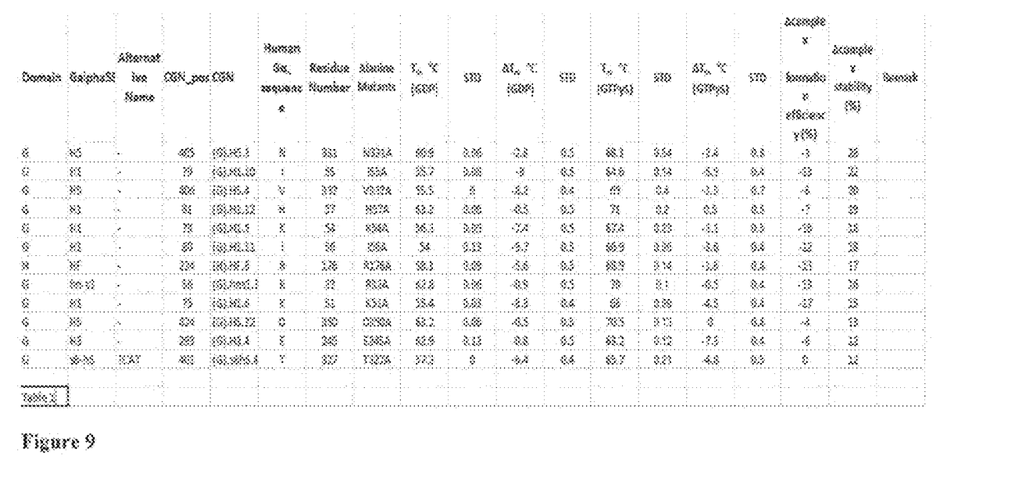
FIG. 9 Table 1 showing twelve Gαi1 mutants having a higher binding ability in the R*-Gi complex as compared to the WT.
Figure 10:
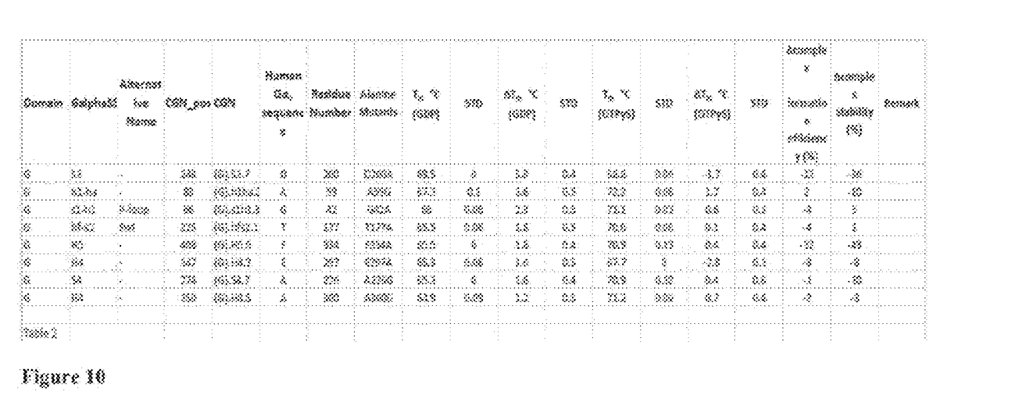
FIG. 10 Table 2 showing eight Gαi1 mutants having a higher capability to stabilize the GDP-bound state as compared to the WT.
Figure 11:
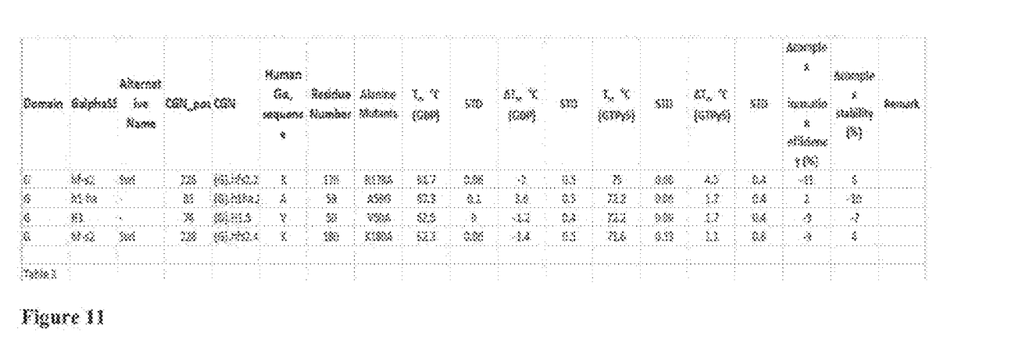
FIG. 11 Table 3 showing four Gαi1 mutants having a capability to stabilize the GTP-bound state as compared to the WT.

While the mutations of the first group (R32G.HNS1.3, K51G.H1.6, K54G.H1.9, I55G.H1.10, I56G.H1.11, H57G.H1.12, R176H.HF.6, E245G.H3.4, T327G.S6H5.4, N331G.H5.3, V332G.H5.4, D350G.H5.22) stabilise the Rho*-G complex and are involved in the activation process, stabilisation or destabilisation of the inter-domain interface, or interactions with the receptor or the βγ subunit (see also Table 1 in FIG. 9), the eight mutations in the second group (G42G.S1H1.3, A59G.H1HA.2, T177G.HFS2.1, D200G.S3.7, A226G.S4.7, E297G.H4.2, A300G.H4.5, F334G.H5.6) contribute to the stabilization of the GDP-bound state (see also Table 2 in FIG. 10, and the four mutations comprised in the third group (V50G.H1.5, A59G.H1HA.2, R178G.HFS2.2, K180G.HFS2.4) stabilize the GTP-bound state (see also Table 3 in FIG. 11).

In order to allow the comparison and extrapolation of the findings to other $G\alpha$ proteins, throughout this application the common G protein numbering system (CGN) proposed in Flock et al., A universal allosteric mechanism for $G\alpha$ protein activation. Nature, 2015. in press, is used. In this system, the superscript next to the residue number denotes: i) either the GTPase (G) or helical (H) domain, ii) the secondary structure element within each domain (e.g., HN for helix N or SI for beta sheet β1), and iii) its position within this structural element (e.g., 1), according to a sequence alignment of 973 G protein sequences. For example, L353G.H5.25 corresponds to the L353 in $G\alpha_{i1}$, GTPase domain, helix 5, and position 25 of the helix 5 in the universal alignment.

The mutations that stabilise the binding to the receptor can be used to facilitate structural and biophysical studies of GPCR-G protein complexes, while the mutations that stabilise the nucleotide-bound states of the $G\alpha$ may be used for studies of the $G\alpha$ complexes with other interacting proteins. It is also possible that these mutations can be used to develop biosensors for the G protein activation with altered properties (eg, slower of faster response, or larger signal change).

BRIEF DESCRIPTION OF THE DRAWINGS

Preferred examples of the present invention are hereinafter described in more detail with reference to the attached drawings which depict in:

FIG. 8 the legend for the Tables 1 to 3 shown in FIGS. 9 to 11;

DETAILED DESCRIPTION OF THE INVENTION

According to the present invention, an alanine scanning study covering 99% of the $G\alpha_{i1}$ sequence was performed and the effects of each amino acid on Rhodopin-$G_i$ complex formation and complex stability, as well as on the stability of GDP and GTPγS (non-hydrolysable analog of GTP)-bound states of $G\alpha_{i1}$ is characterized. Comparison of the effects contributed by each residue provide one functional map of Gα subunit in inactive and active conformations, which significantly extending the understanding of the G protein activation process. The alanine scanning study has been systematically executed as HTP assay for monitoring effects of $G\alpha_{i1}$ alanine mutants in R*-$G_i$ complex. The recombinant alanine mutants were prepared by HTP purification and the endogenous rhodopsin and βγ subunit were prepared from bovine retinas. For formation of R*_Gi complex, Gαi1 and βγ subunit were reconstituted to Gi heterotrimer, followed by mixing with rhodopsin and light activation. The formed R*_Gi complexes were visualized by native gel electrophoresis and the gel bands of complexes were quantified by ImageJ software. In each round, wild-type $G\alpha_{i1}$ was always included as reference control.

To examine how each single alanine mutant of $G\alpha_{i1}$ responses to rhodopsin-mediated activation, a novel HTP screening assay based on native gel electrophoresis (NPAGE) was developed by which the relative amount (see methods) and the relative stability (see methods) of activated rhodopsin-bound complex (R*-$G_i$) constituted with each alanine mutant of $G\alpha_{i1}$ could be measured and compared. The most interesting results are shown in Tables 1 to 3 provided in FIGS. 9 to 11.

FIG. 8 shows the legend for a better understanding of FIGS. 9 to 11. The tables show for example the residue number that has been replaced with alanine if the amino acid at that position is a non-alanine residue and has been replaced with glycine if the amino acid at that position is an alanine residue. The tables further comprise the experimental data on the thermostability of the GDP and GTPγS bound states of the $G\alpha_{i1}$, the data on the complex formation efficiency relative to the wt $G\alpha_{i1}$ and the stability of the complex after incubation at elevated temperature, again relative to the complex of rhodopsin with wt $G\alpha_{i1}$. A detailed description of the experimental procedures and the definition of the complex stability is provided in the Section Materials and Methods.

Figure 2:
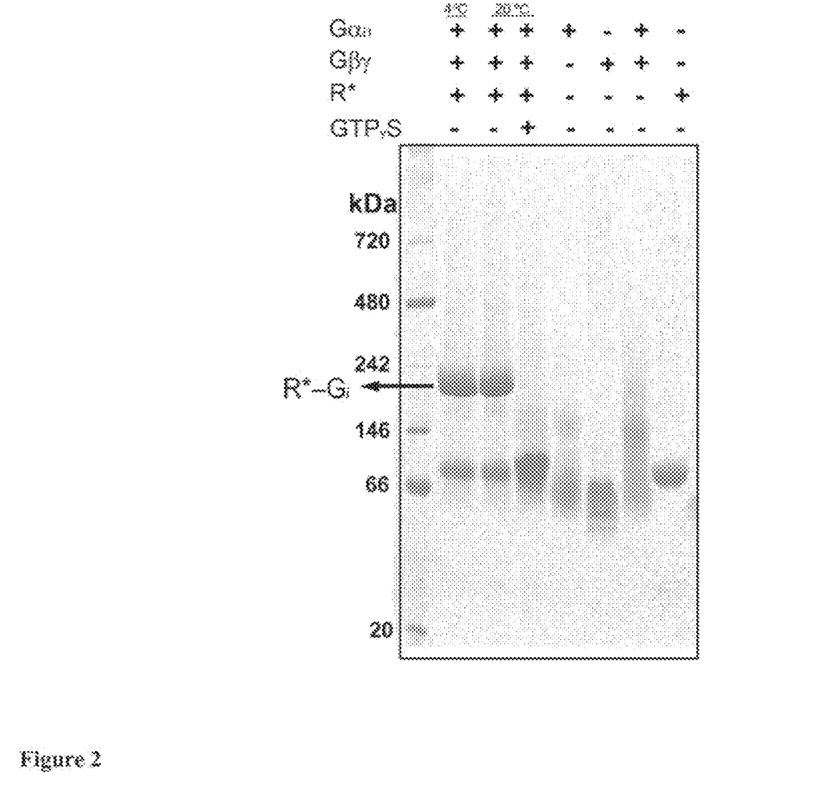
FIG. 2 a visualization of R*_Gi (WT) complex by native gel electrophoresis.

Meanwhile, to compare together with nucleotide-bound state, the thermal stability of each single alanine mutant of $G\alpha_{i1}$ was measured in addition of GDP or GTPγS (see also FIG. 2).

FIG. 2 shows a visualization of R*_Gi (WT) complex by native gel electrophoresis. The displayed R*_Gi complex was formed with wild-type Gαi1 as described in methods and FIG. 1. To further confirm the complex, the R*_Gi (WT) was incubated with 100 µM GTPγS at 20° C. for 1 hour. The R*_Gi (WT) complex (+/−GTPγS) were visualized by native gel electrophoresis, as well as WT Gαi1, βγ subunit, Gαi1βγ heterotrimer, and activated rhodopsin as reference markers. It clearly shows that the R*_Gi complex with "empty-pocket" becomes disassociated in addition of GTPγS.

Figure 3:
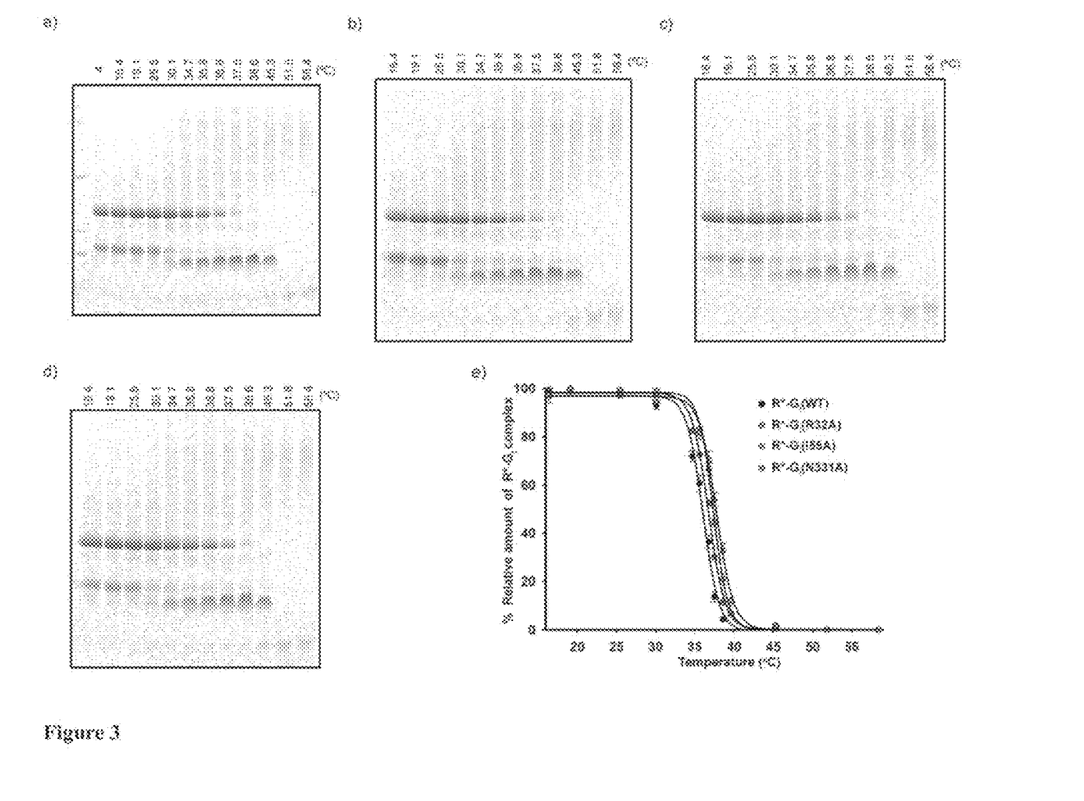
FIG. 3 the monitoring of the thermal dissociation (Td) of R*-Gi complex by native gel electrophoresis.

FIG. 3 illustrates the monitoring of the thermal dissociation (Td) of R*-Gi complex by native gel electrophoresis. The formation of R*_Gi complex was performed as described in methods and FIG. 1. The R*_Gi complex formed with wild-type Gαi1 (a), R32A (b), I55A (c) or N331A (d) were heated in the indicated temperature and the heated samples were visualized by native gel electrophoresis; e) The relative amount of complex at each temperature was normalized (0-100%) to the amount of complex at 16.4° C. and fitted with sigmoidal Boltzmann equation to obtain Td50 values. The determined Td50 of R*_Gi (WT) is 36.0±0.12° C. The Td50 of R*_Gi (R32A), R*_Gi (I55A) and R*_Gi (N331A) are 36.7±0.08° C., 37.4±0.05° C. and 37.8±0.08° C., respectively. Data points represent mean±s.d. from three individual experiments.

Figure 4:
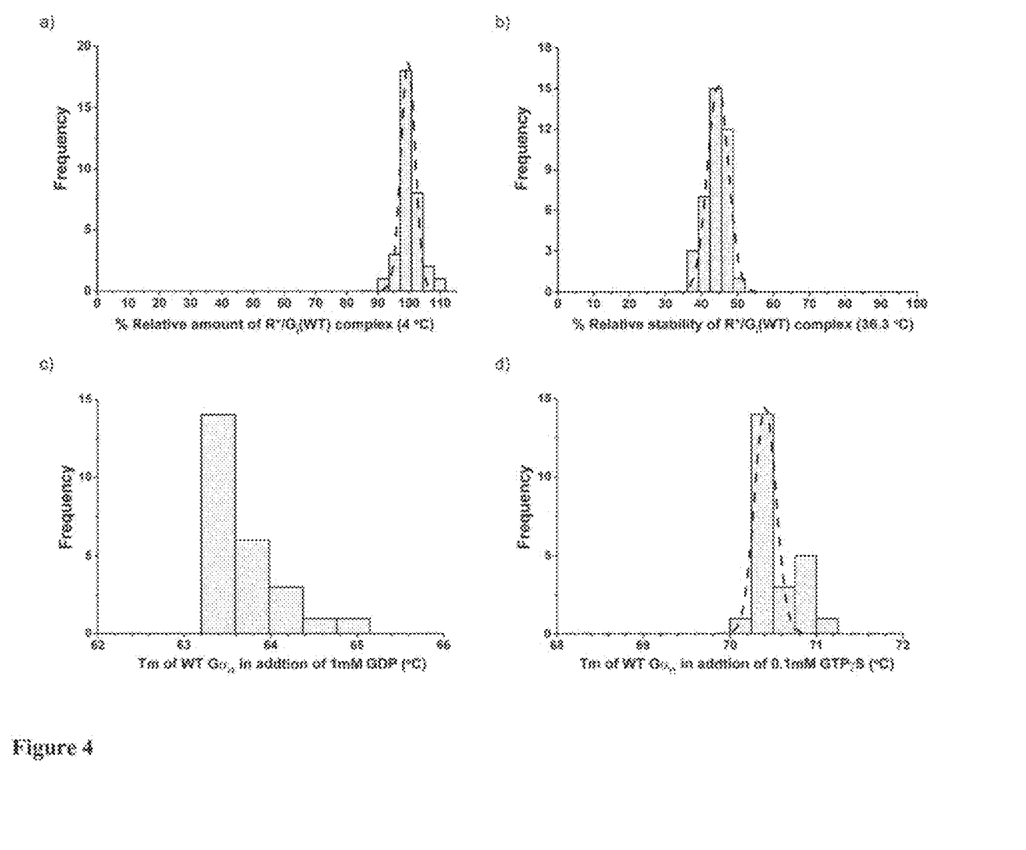
FIG. 4 a statistics analysis of R*-Gi (WT) complex and Tm of WT G$\alpha$i1-GDP or GTPγS.

FIG. 4 shows a statistics analysis of R*-Gi (WT) complex and Tm of WT Gαi1-GDP or GTPγS. The formation of R*-Gi (WT) complex with wild-type Gαi1 and measurement of Tm were performed as described in methods and FIG. 1. a) The relative amount of R*-Gi (WT) at 4° C. was derived from 33 individuals measurements. The mean is 100±3.61%. The individual values are grouped in intervals with widths of 3.61% and are shown in their frequency. The frequency distribution is fitted with Gaussian model (dotted line) with an R2 of 0.9839. b) The relative stability of R*-Gi (WT) at 36.3° C. was determined from 38 individual measurements with the mean of 43.9±3.20%. The fitted frequency distribution with Gaussian model is with an R2 of 0.9631. The frequency distributions of Tm of WT Gαi1 in addition of 1 mM GDP and 0.1 mM GTPγS are shown in (c) and (d) from 25 and 24 individual measurements, respectively. The mean of Tm of WT Gαi1-GDP or GTPγS are 63.68±0.39° C. and 70.51±0.26° C.

Figure 1:
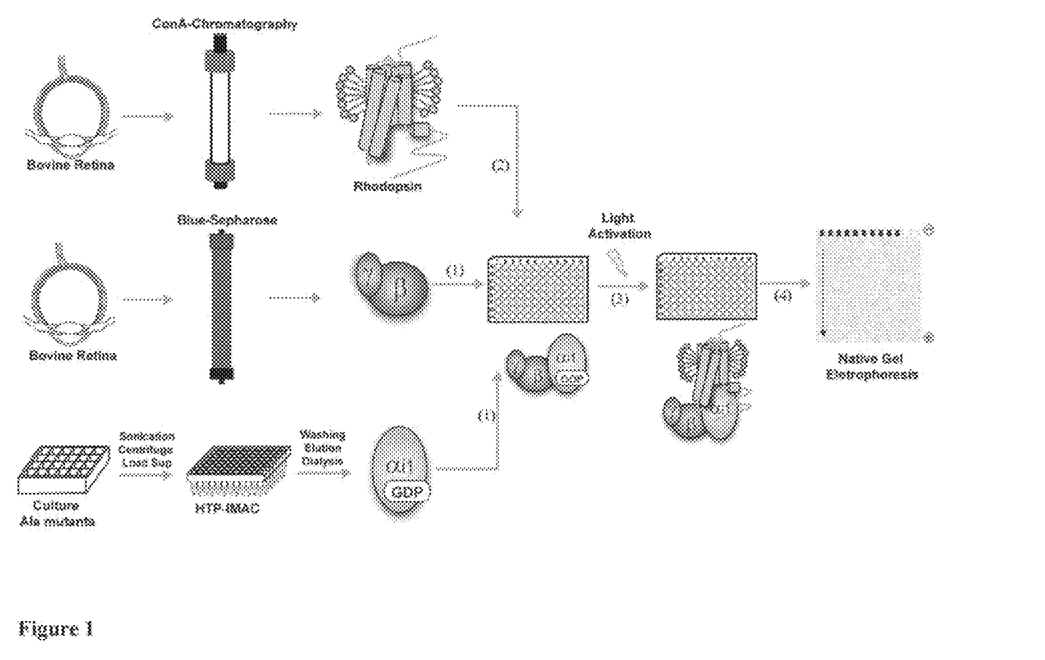
FIG. 1 schematically an HTP assay for monitoring effects of G$\alpha$i1 alanine mutants in R*-Gi complex.
Figure 5:
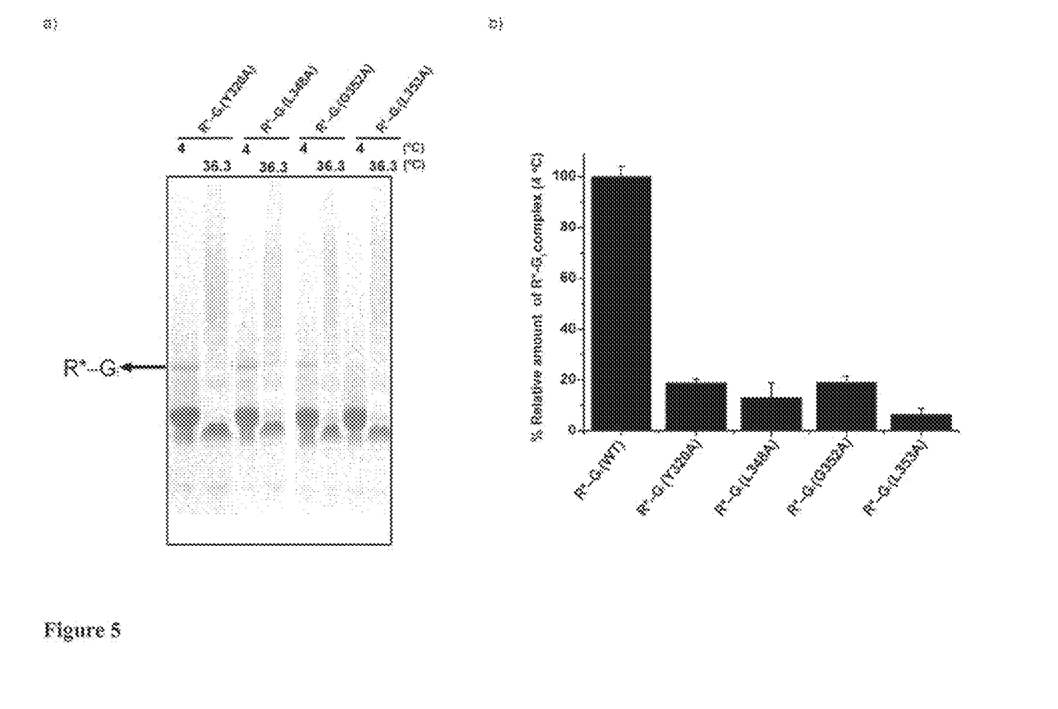
FIG. 5 a characterization of G$\alpha$i1 alanine mutants impaired in formation of R*-Gi complex.

FIG. 5 depicts a characterization of Gαi1 alanine mutants impaired in formation of R*-Gi complex. a) The formation of R*-Gi complex with Y320A, L348A, G352A and L353A of Gαi1 were performed as described in methods and FIG. 1. The formed complexes were heated at 36.3° C. The R*-Gi complex at 4° C. and the heated R*-Gi complex at 36.3° C. were visualized by native gel electrophoresis. b) The amounts of complexes were determined by quantifying the gel bands of complex with ImageJ software. The relative amount of complex (%) at 4° C. is normalized to the amount of R*-Gi (WT) complex. Data points represent mean±s.d. from three individual experiments. The assay clearly shows that these four alanine mutants are severely impaired in formation of R*-Gi complex.

Figure 6:
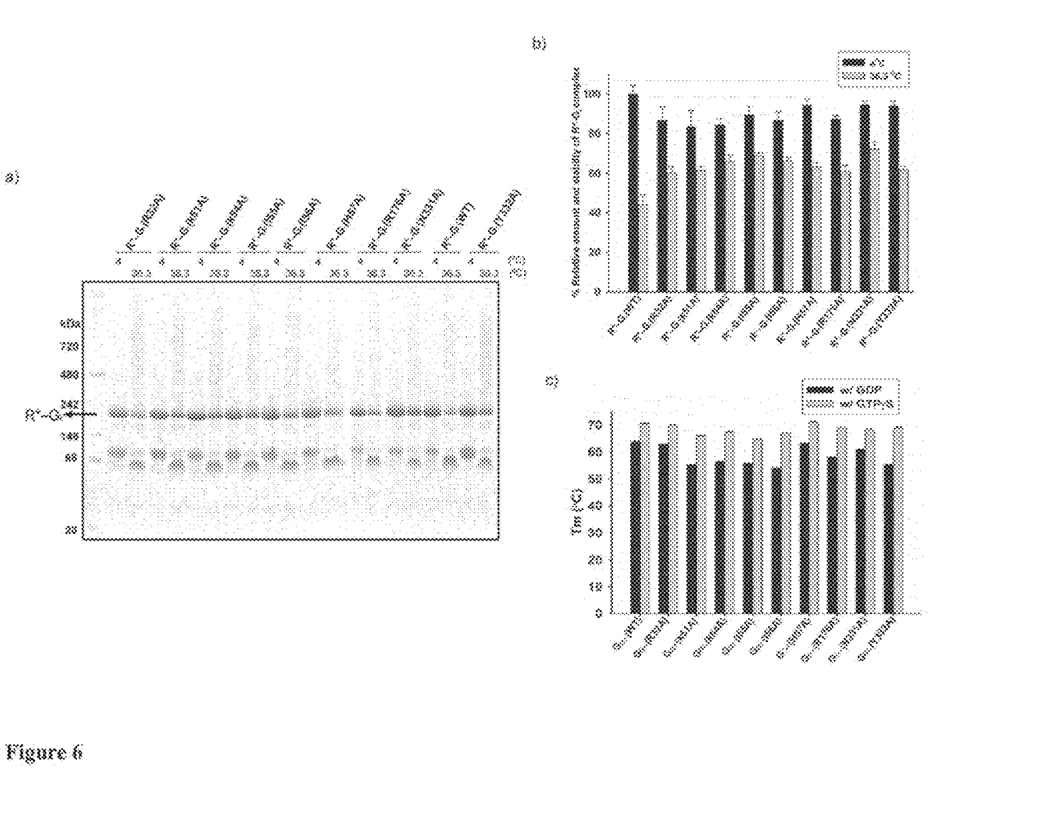
FIG. 6 a characterization of G$\alpha$i1 alanine mutants stabilizing the R*-Gi complex.

FIG. 6 illustrates a characterization of Gαi1 alanine mutants stabilizing the R*-Gi complex. a) The formation of R*-Gi complexes were proceeded as described in methods and FIG. 1. The formed complexes were heated at 36.3° C. Then, the R*-Gi complex at 4° C. and the heated R*-Gi complex at 36.3° C. were visualized by native gel electrophoresis. b) The amounts of complexes were determined by quantifying the gel bands of complex with ImageJ software. The relative amount of complex (%) at 4° C. and relative stability of complex (%) at 36.3° C. were determined as described in methods. The result shows that these alanine mutants of Gαi1 obviously enhance the thermostability of R*-Gi complex. c) Tm of Gαi1 alanine mutants in additions of nucleotides (1 mM GDP or 0.1 mM GTPγS) were determined by DSF assay. Data points represent mean±s.d. from three individual experiments.

Figure 7:
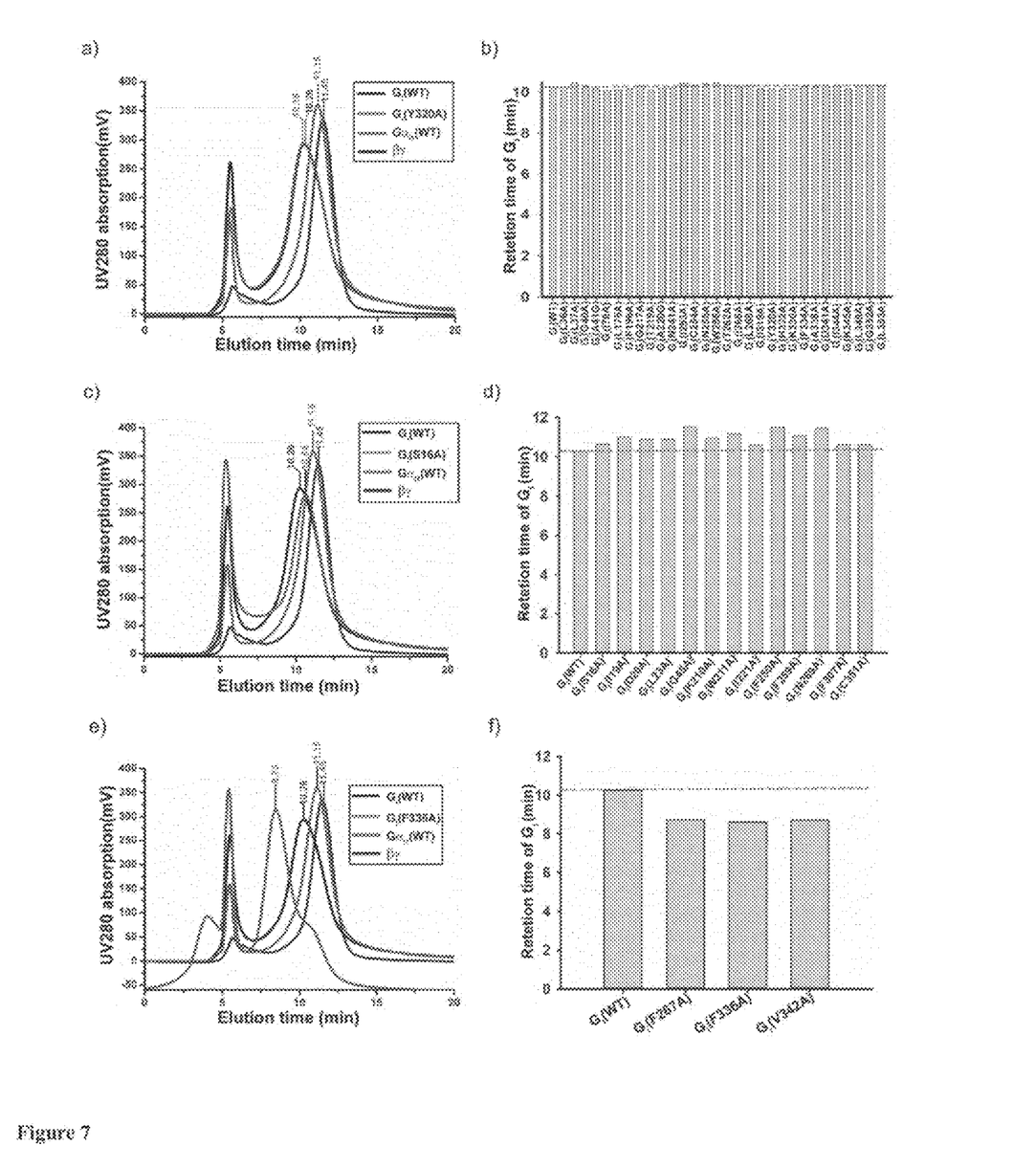
FIG. 7 a characterization of heterotrimer (Gi) formation by analytical size-exclusion chromatography (FSEC)

FIG. 7 represents a characterization of heterotrimer (Gi) formation by analytical size-exclusion chromatography (FSEC). The last 48 alanine mutants which are not efficient in formation of R*-Gi complex are reconstituted with βγ subunit to form Gi and characterized by FSEC as described in methods. The retention time of WT Gαi1, βγ subunit and reconstituted Gi are 11.15 min, 11.45 min and 10.26 min, respectively. a) and b) show the retention time of alanine mutants which are efficient in heterotrimer reconstitution. The inefficient alanine mutants in formation of heterotrimer are displayed in c) and d). Three alanine mutants forming oligomer reconstitution are shown in e) and f).

While the mutations of the first group (R32G.HNS1.3, K51G.H1.6, K54G.H1.9, I55G.H1.10, I56G.H1.11, H57G.H1.12, R176H.HF.6, E245G.H3.4, T327G.S6H5.4, N331G.H5.3, V332G.H5.4, D350G.H5.22) stabilise the Rho*-G complex and are involved in the activation process, stabilisation or destabilisation of the inter-domain interface, or interactions with the receptor or the βγ subunit (see also Table 1 in FIG. 9), the eight mutations in the second group (G42G.S1H1.3, A59G.H1HA.2, T177G.HFS2.1, D200G.S3.7, A226G.S4.7, E297G.H4.2, A300G.H4.5, F334G.H5.6) contribute to the stabilization of the GDP-bound state (see also Table 2 in FIG. 10, and the four mutations comprised in the third group (V50G.H1.5, A59G.H1HA.2, R178G.HFS2.2, K180G.HFS2.4) stabilize the GTP-bound state (see also Table 3 in FIG. 11.

In order to allow the comparison and extrapolation of the findings to other Gα proteins, throughout this application the common G protein numbering system (CGN) proposed in Flock et al. [1] is used. In this system, the superscript next to the residue number denotes: i) either the GTPase (G) or helical (H) domain, ii) the secondary structure element within each domain (e.g. HN for helix N or S1 for beta sheet β1), and iii) its position within this structural element (e.g. 1), according to a sequence alignment of 973 G protein sequences. For example, L353G.H5.25 corresponds to the L353 in Gαi1, GTPase domain, helix 5, and position 25 of the helix 5 in the universal alignment.

Numerous studies have demonstrated that the last 11 residues in c-terminus of Gα play the critical role in recognizing and anchoring cognate receptors. Not surprisingly, the present assays also show the consistent results that many alanine mutants in last 11 amino acids (344-354aa) of Gα$_{i1}$ significantly affect the formation of R*-G$_i$ complex, especially alanine substations of two invariantly conserved residues (L348 and L353) and G352 in extreme c-terminus of Gα$_{i1}$ which are severely impaired in coupling with receptor. The thermal stability results also clearly show that these alanine mutants do not affect stability of nucleotide-bound state, but dramatically destabilize (except D350) the receptor-bound state, indicating the local conformational changes in c-terminus of Gα$_{i1}$ induced by activated rhodopsin. It is well agreed with structures of rhodopsin coupled with c-terminal peptide of Gα and crystal structure of β$_2$AR/G$_s$ in which c-terminus of Gα reforms to alpha-helix from disordered loop and penetrates into the cytoplasmic core of transmembrane bundle of GPCRs.

In receptor-mediated response, except c-terminus of Gα undergoes disorder-to-order conformational change, another substantially conformational alteration in GTPase domain is shown in α5-helix with obvious rigid body rotation and translation. The results clearly show that the movement of α5-helix need interrupt one intracellular stabilization network in GTPase domain of nucleotide-bound Gα$_{i1}$, simultaneously, the relocated residues in α5 need quickly form the rearranged intracellular network to further stabilize both GTPase domain and R*-G$_i$ complex conformation. The observed intracellular network in GTPase domain of Gα$_{i1}$ can be regarded as two subnetworks centred with beta sheet sandwich (β4, β5 and β6).

The subnetwork in GTPase domain which is characterized with dynamic alternations in conformation is surrounded by six-stranded β sheet, α1 and α5. In nucleotide-bound state of Gα$_{i1}$, this subnetwork is mainly formed by many highly conserved hydrophobic residues from β1-3 strands, α1-helix and inward residues of α5-helix. Alanine substitutions of these hydrophobic residues significantly destabilize GDP-bound conformation (4-18° C.) and mildly destabilize GTPγS-bound state (2-5° C.). Especially, alanine replacement of F336 (invariantly conserved in Gα subfamilies) in α5-helix which is relocated to contact with IC2 loop of GPCR severely impairs Gα$_{i1}$ to couple with nucleotides (Table 1), indicating that the relocation of F336 will cause dramatically destabilization of nucleotide-bound Gα conformation.

Upon interaction with activated receptor, on the one hand, the present stability results show that the subnetwork in nucleotide-bound state of Gα$_{i1}$ is rearranged by dramatically weakening contacts with α1: alanine mutations of residues (I49, M53, and I56 in α1, L38 of (β1, T329 and V332 of α5) which are involved to tether α1 in Gα$_{i1}$-GDP severely impair the stability of Gα$_{i1}$-GDP, whereas they do not affect the relative stability of R*-G$_i$ complex. Especially, N331A (invariantly conserved) and adjacent V332A (highly conserved) in α5 obviously enhance the relative complex stability by 18% and 28%, respectively (Table 1, FIG. 6), indicating that the position of relocated N331 and V332 in α5 is characterized with apparent flexibility.

Although it cannot completely concluded that the loose of helicity at the base of the α5-helix observed in β$_2$AR/G$_s$ is caused by losing contact with α1 or by the relocation of N331 and V332, the order-to-disordered transition in N-terminus of α5-helix will increase the flexibility of TCAT loop and facilitate the interruption between the adjacent TCAT site and GDP.

On the other hand, the receptor-mediated response reforms the subnetwork in nucleotide-bound state of Gα$_{i1}$ by strengthening the interaction with β4 and β5: alanine mutations of new introduced residues (I265 of β4, Y320 and H322 of β5, F334, V335, V339 and V342 of α5) are characterized with dramatically destabilizing the R*-G$_i$ complex (19-45%), whereas not affecting the stability of nucleotide-bound state (Table 1).

Interestingly, in this subnetwork, alanine mutations of many residues which are important for stabilizing nucleotide-bound conformation do not affect the R*-G$_i$ complex formation (Table 1). However, except V335A and V339A, alanine replacements of all the new included residues (I265 of β4, Y320 and H322 of β5, F334 and V342 of α5) obviously form less amount of R*-G$_i$ complex (18-78% of WT level) (Table 1). To exclude the possibility that the insufficient formation of R*-G$_i$ complex (less than 20% of WT level) may be caused by inefficient heterotrimer reconstitution, the efficiency of heterotrimer reconstitution with βγ subunit has been examined (See methods). The results show that the new involved residues are characterized with the similar ability of WT upon formation of heterotrimer (see FIG. 7), indicating that these residues play the critical role in allosteric activation of G protein upon receptor response.

Especially, alanine substitution of Y320 (invariantly conserved in Gα subfamilies) in β5 severely impairs the R*-G$_i$ complex formation (see FIG. 5). In the whole alanine scanning, except three alanine mutants (L348A, G352A and L353A) in extreme c-terminus of Gα$_{i1}$ impairing in complex formation, Y320A is the only one alanine mutant which does not directly interact with receptor, whereas it is deficient in coupling with activated rhodopsin (FIG. 5). It can be predicted that Y320 is one critical signal receiver and transmitter in receptor-mediated G protein activation. Indirectly, it implicates that Y320A may still be able to utilize the well-conserved L348, G352 and L353 in c-terminus of Gα$_{i1}$ to couple with receptor and form the "pre-coupled" R*-G$_i$ (GDP). However, the "pre-coupled" conformation can be instantaneously disassembled because Y320A blocks the signal of GDP release transmitted from receptor. The previous researches also showed the existence of "pre-coupled" receptor complex in vivo and in vitro.

Moreover, in GTPase domain, another observed subnetwork harboured by beta sheet sandwich, α3, α4 and αG utilize many highly conserved hydrophobic residues to form hydrophobic interactions which stabilize both nucleotide-bound and receptor-bound conformations. Among those residues, many alanine mutants are characterized with obvious destabilization in GDP-bound state from 3 to 13° C. (ΔTm) and receptor-bound state from 30 to 40% (Δ relative complex stability), as well as mild destabilization in GTPγS-bound state (1-5° C.) (Table 1). Additionally, the relative amount of R*-G$_i$ complex formed with many alanine mutants in this subnetwork is also less than 10-56% of WT level (Table S1). The results of heterotrimer reconstitution demonstrate that F250A (α3), L266A, L268A (β5) and I319A (β6) show the comparable ability relative to WT in coupling with βγ submit. Since these residues are located far from the receptor binding interface, it suggests that they may also be involved in the allosteric activation of G protein and alanine mutation may affect the signal of GDP release transmitted from receptor.

Upon formation of GPCR/G complex, HD domain was observed to be largely displaced again GTPase domain and stay in dynamic equilibrium with multiple conformations. The present stability results show that many hydrophobic residues in HD domain of Gα$_{i1}$ form hydrophobic core packing to stabilize both nucleotide-bound and receptor-bound conformations. The sequence alignment result shows that these hydrophobic residues are highly conserved in Gα subtypes. It indicates that the observed inherent hydrophobic core packing can be supposed to play the critical role in stabilizing the dynamic conformations of HD domain in receptor-bound state. Especially, alanine mutants in αE obviously destabilize R*-G$_i$ conformation, without affecting the stability of nucleotide-bound states, suggesting that the subtly internal-arrangement in HD domain is required to keep the integrity of displaced HD domain and stabilize the "empty-pocket" conformation of R*-G$_i$ complex.

Furthermore, in the present binding assay with R*, except I78A of αA and L175A of αF show mild decrement (20%) in R*-G$_i$ complex formation, all alanine mutants in HD (63aa-176aa) of Gα$_{i1}$ form highly comparable R*-G$_i$ complex (90-100% of WT level), implicating that helical domain in receptor-regulated response may function as one passive participant which exits with independent integrity without affecting overall ability of Gα subunit to couple with receptor.

Another hallmark of G protein activation by receptors is to release GDP accompanied with separation between GTPase domain and HD domain. The stability results of interdomain interface in Gαi1 (composed by N-terminal of αA, αF and α1) reveal that alanine mutations of involved residue dramatically destabilize GDP-bound state (5-14° C.), whereas they do not affect the relative stability of R*-Gi complex.

The sequence alignment displays that the residues located in interdomain interface of Gαi1 are highly conserved in Gα subfamilies. It implicates that any subtle conformational perturbations are possible to cause the destabilization in interdomain interaction of Gα-GDP, which will facilitate the domain separation in Gα subunit and release GDP. Interestingly, K51A, K54A and I55A of α1 obviously increase the relative R*-Gi complex stability by 17%, 22%, and 25% of WT level, respectively. The similar scenario is also observed in L175A and adjacent R176A in N-terminus of αF by increment in relative complex stability of 9% and 17%.

The enhanced stability in R*-Gi complex can be ascribed as decreasing the flexibility of areas composed by these residues, which is consistent with crystal structure of β2AR/Gs in which top of αA and loop connected with N-terminus of αF in Gsα is disordered and invisible in structure. It indicates that the flexibility shown in N-terminus of αF and top of αA can be one intrinsic character and they function as hinge together with loop regions to allow a range of dynamic motion of HD domain in receptor-mediated response.

Alternatively, the present results highlight the discriminate stability character of α1-helix in Gα$_{i1}$: alanine replacement of residues in α1-helix (46-57aa) severely destabilizes GDP-bound conformation (except S47A, V50A and H57A), but not affects the relative stability of receptor-bound conformation (except Q52A) (FIG. 6), conversely, alanine mutants located in the top of α1 significantly enhance the relative complex stability. It is consistent with enhanced hydrogen exchange observed in α1-helix of Gsα in β2AR-mediated response by DXMS analysis. Additionally, the sequence alignment shows that α1-helix is completely conserved in Gα subfamilies as KST (I/F) (V/L/I) KQM (K/R) I (I/L) H, among of which conserved KST sequence is part of prominent P-loop.

Collectively, it can conclude that α1-helix functions as a central hub in nucleotide-bound conformation, which plays the predominant role in stabilizing GTPase domain together with linked α5-helix, tethering interdomain interaction and encapsulating the bound-nucleotide. Particularly, α1-helix is existence in metastable status in GDP-bound conformation. Once upon coupling with receptor, the distortion of α5-helix dramatically interrupts the interaction with α1-helix, which causes the transition of α1-helix from metastable status to super-unstable status. Consequentially, it leads domain separation and GDP release.

In summary, alanine scanning method is used to provide the first complete molecular mapping of Gα$_{i1}$ subunit in both nucleotide and receptor-bound states at each single residue resolution (FIG. 1 and Table 1). The present results clearly reveal that Gαi1 subunit utilizes many highly conserved residues to form one global interaction network which stabilizes different conformational states and regulate the allosteric activation of Gi protein. Based on the observations, it can be expected that receptors firstly sense the disordered α-terminus of Gα subunit in GDP-bound state. Once c-terminus of Gα subunit is trapped into receptor, it forms "pre-coupled" R*-G (GDP) conformation. Simultaneously, the signal of GDP release transmitted from receptors is propagated to Gα protein through unvaried tryptophan (β5), which triggers the formation of allosteric activation network through the rotation and translation of α5-helix. The relocation of α5-helix causes the dismantlement of N-terminus of α5 to increase the flexibility of TCAT loop, as well as dramatically interrupts the interactions of α1. The perturbations in α1 lead the metastable α1 to become apparently unstable, which further destabilise the interdomain interface and P-loop. While N-terminal of α1 completes order-to-disordered transition, HD domain is also completely displaced against GTPase domain accompanying with the release of GDP.

Section Materials and Methods

1) Alanine Scanning Mutagenesis.

The alanine scanning expression library of $G\alpha_{i1}$ was prepared as reported before, D. Sun, et al., AAscan, PCRdesign and MutantChecher: a suite for programs for primer design and sequence analysis for high-throughput scanning mutagenesis. PLoS ONE, 2013. 8(10): p. e78878. The wild-type (WT) plasmid was constructed by inserting human G protein alpha-subunit ($G\alpha_{i1}$) into pJ411 vector (DNA 2.0) which incorporated a N-terminal 10-histidine tag followed by a TEV cleavage site. The alanine mutants were produced based on the WT plasmid by high-throughput (HTP) alanine mutagenesis as reported previously (Sun et al.). All 354 amino acid residues in $G\alpha_{i1}$ were mutated. All non-alanine residues were replaced to alanine and alanine residues were substituted to glycine. The protein sequence of the construct used in the experiments was SEQ ID NO:1 set forth below:

MKKHHHHHHHHHHENLYFQGGSMGCTLSAEDKAAVERSKMIDRNLREDGE

KAAREVKLLLLGAGESGKSTIVKQMKIIHEAGYSEEECKQYKAVVYSNTI

QSIIAIIRAMGRLKIDFGDSARADDARQLFVLAGAAEEGFMTAELAGVIK

RLWKDSGVQACFNRSREYQLNDSAAYYLNDLDRIAQPNYIPTQQDVLRTR

VKTTGIVETHFTFKDLHFKMFDVGGQRSERKKWIHCFEGVTAIIFCVALS

DYDLVLAEDEEMNRMHESMKLFDSICNNKWFTDTSIILFLNKKDLFEEKI

KKSPLTICYPEYAGSNTYEEAAAYIQCQFEDLNKRKDTKEIYTHFTCATD

TKNVQFVFDAVTDVIIKNNLKDCGLF*

The amino acid numbers refer to the positions in the WT protein (starting MGC . . . ).

2) Preparation of native βγ subunit (Gβγ).

Gβγ was separated from endogenous transducin (Gt) as previously described S. Maeda, et al., Crystallization scale preparation of a stable GPCR signaling complex between constitutively active rhodopsin and G protein. PLoS ONE, 2014. 9(6): p. e98714. Briefly, dark-adapted bovine retinas (W L Lawson, USA) were exposed to room light at 4° C. overnight. The rod outer segment (ROS) membranes were collected by centrifugation in a 25-30% (w/w) sucrose gradient. After isotonic and hypotonic washes, Gt was dissociated from ROS membrane by adding GTP (Sigma-Aldrich). The collected Gt was filtered through 0.22 µm membrane (Millipore Corp) and dialyzed against the dialysis buffer (10 mM Tris-HCl, pH 7.4, 2 mM MgCl2, 1 mM DTT) containing 50% glycerol. Gβγ was further separated from the Gαt on a Blue-Sepharose column (GE Healthcare) by a linear salt gradient (0-500 mM NaCl) in the dialysis buffer supplemented with 30% glycerol. The Gβγ was concentrated to 1-5 mg/ml and stored at −80° C.

3) Preparation of Bovine Rhodopsin.

Bovine rhodopsin was extracted from dark-adapted ROS membranes which were prepared according to known Okada's method. The dark-adapted ROS membranes were solubilized in solubilization buffer (50 mM sodium acetate, pH 6, 1 mM EDTA, 2 mM 2-mercaptoethanol, 3 mM CaCl2, 3 mM MgCl2, 3 mM MnCl2, 100 mM NaCl) supplemented with 80 mM (4.1%) β-dodecyl-D-n-maltoside (DDM) at 4° C. overnight. After centrifugation at 30,000 rpm in a Ti70 rotor, the supernatant was diluted with solubilisation buffer to a concentration of DDM as 0.4%. The diluted sample was loaded to a column packed with ConA Sepharose resin (GE Healthcare) which was equilibrated with washing buffer (solubilisation buffer supplemented with 0.02% DDM). After extensive washing, bovine rhodopsin was eluted with solubilisation buffer supplemented with 0.02% DDM and 0.2 M α-D-methylmannoside. The eluted bovine rhodopsin was concentrated to 1-4 mg/ml and stored at −80° C.

4) High Throughput (HTP) Culturing and Purification of Gαi1 Alanine Mutants.

The recombinant Gαi1 alanine mutants were expressed in BL21 (DE3) competent cells. The cultures were grown at 37° C. in TB media (GERBU Biotechnik GmbH) by using 24 well plates (mutant/well) (Whatman UniFilter Microplates, GE Healthcare). The culture volume was 5 ml/well. When the OD600 reached 0.6, cells were induced with 0.5 mM IPTG and continued to grow for 20 hours at 20° C. The cell were harvested by centrifugation resuspended in the binding buffer (25 mM Tris-HCl, pH 7.4, 500 mM NaCl, 10% glycerol, 50 mM imidazole, 5 mM 2-mercaptoethanol) and transferred to a 96 deep-well plate (Thermo Scientific). The re-suspended cells were disrupted by sonication for 1 min using a SONICS VCX-600 sonicator equipped with an 8-pin probe.

After clarifying cell lysates by centrifugation, the supernatants were loaded to a 96 deep-well filter plate (one mutant per well) pre-loaded with 500 µl cobalt chelating resin (GE Healthcare) and equilibrated with binding buffer. After extensive washing with binding buffer, the recombinant Gαi1 alanine mutants were eluted with elution buffer (25 mM Tris-HCl, pH 7.4, 500 mM NaCl, 10% glycerol, 500 mM imidazole, 5 mM 2-mercaptoethanol). The eluted proteins were dialyzed against 25 mM Hepes, pH 7.4, 100 mM NaCl and 2 mM DTT using Slide-A-Lyzer MINI Dialysis Device (Thermo Scientific). Among of 354 alanine mutants, the purified R142AH.HD.9, Y230AG.s4h3.4, K270AG.s5hg.1 and D272AG.HG.2 were severely aggregated and could not be used in the further assays. The flowchart of HTP purification is shown in FIG. 1.

5) Characterization of the Effect of Gαi1 Alanine Mutants on the Receptor-Bound State by a HTP Assay.

In each round, WT Gαi1 was always prepared in parallel with the Gαi1 alanine mutants [Gαi1(Ala)] to form rhodopsin-Gi protein complex [Rho*-Gi(WT)] as the reference control. The recombinant Gαi1 alanine mutants (12.5 µM) from HTP purification and the native Gβγt (10 µM) were reconstituted to form heterotrimer (Gi) by incubation in a 96-well PCR plate (one mutant per well) (Eppendorf) on ice for 2 h. Under the dim-red light in the dark room, purified rhodopsin (18 µM) was added and mixed with Gi in ice-cold assay buffer (25 mM Hepes, pH 7.4, 100 mM NaCl, 2 mM DTT, 0.02% DDM, 1 mM MgCl2, 0.16 unit/ml apyrase). After irradiation with orange light (>495 nm) on ice for 10 min, the tetramer complex Rho*-Gi(Ala) was formed by coupling the activated rhodopsin with Gi and the formed Rho*-Gi(Ala) complex was further incubated in the dark at 4° C. overnight. The reaction volume was 50 µl for each alanine mutant. 20 µl of each Rho*-Gi(Ala) complex was transferred to another 96-well PCR plate and heated for 30 min in a PCR machine (Eppendorf Mastercycler Gradient) at 36.3° C. After centrifugation at 3000 rpm for 10 min at 4°

C., 14 µl of formed Rho*-Gi(Ala) complex (4° C.) and 14 µl of heated Rho*-Gi(Ala) complex (36.3° C.) were mixed with NativePAGE Sample Buffer (4×) (Invitrogen) and NativePAGE 5% G-250 Sample Additive (Invitrogen), respectively. The mixtures were loaded onto 4-16% Native-PAGE Bis-Tris-HCl Gels (Invitrogen) and gel electrophoresis was performed in a 4° C. cold room according to the manufacturer's protocol (Invitrogen). Protein markers were used with NativeMark Unstained Protein Standard (Invitrogen). The gel bands of Rho*-Gi complex were integrated and quantified using the ImageJ software. The complex formation efficiency (CF) (%) was obtained from the normalization of integrated density of Rho*-Gi complex band [IDC(Ala or WT), 4° C.] with integrated density of Rho*-Gi(WT) complex band [IDC(WT), 4° C.]. The complex stability (CS) (%) was defined as the normalization of integrated density of Rho*-Gi complex band [IDC(Ala or WT), 36.3° C.] with integrated density of Rho*-Gi(WT) complex band [IDC(Ala or WT), 4° C.].

$$CF(Ala) = \frac{ID_c(Ala, 4° C.)}{ID_c(WT, 4° C.)} \times 100\%$$

$$CS(WT) = \frac{ID_c(WT, 36.3° C.)}{ID_c(WT, 4° C.)} \times 100\%$$

$$CS(Ala) = \frac{ID_c(Ala, 36.3° C.)}{ID_c(Ala, 4° C.)} \times 100\%$$

The ΔCF (%) and ΔCS (%) were defined as:

ΔCF=CF(Ala)−CF(WT)

ΔCS=CS(Ala)−CS(WT)

The distribution and summary of ΔCF efficiency and ΔCS of each Gαi1 alanine mutant are listed in FIG. 2 and Table 1. The flowchart diagram of HTP assay is shown in FIG. 1.

6) HTP Measurements of Thermal Stability Gαi1 Alanine Mutants by Differential Scanning Fluorimetry (DSF).

The thermostability of each Gαi1 alanine mutant in the nucleotide-bound states was measured by HTP differential scanning fluorimetry (DSF). The samples were prepared on ice. 10 µl of recombinant Gαi1 alanine mutant stocks (0.7 µg/µl) were dispensed into a 96-well PCR plate (one mutant per well) (Eppendorf) and mixed with 100 µl ice-cold assay buffer (25 mM Hepes, pH 7.4, 100 mM NaCl, 2 mM DTT) containing 5×SYPRO-orange (Invitrogen) and nucleotides (1 mM GDP or 100 µM GTPγS). After mixing, 110 µl reaction mixture of each alanine mutant was divided into 0.2 ml PCR tubes (Qiagen) as three samples of 35 µl. The DSF experiments were performed with Rotor GeneQ (Qiagen) by ramping from 25° C. to 95° C. at a rate of 3° C./min. The melting temperature (Tm) was defined as the inflection point of the melting curve as analysed by the Rotor Gene Q Series Software. The Tm value of each Gαi1 alanine mutant [Tm(Ala)] upon addition of the nucleotides was averaged from three individual experiments. The ΔTm value was defined as:

ΔTm=Tm(Ala)−Tm(WT)

In each round, WT Gαi1 was always prepared in parallel with Gαi1 alanine mutants as a reference control.

In addition, the thermal shift of WT Gαi1 in titration with GDP and GTPγS were also performed with HTP DSF.

7) Analysis of Heterotrimer Formation by Fluorescence Assisted Size Exclusion Chromatography (FSEC)

The recombinant Gαi1 alanine mutants (6 µM) and Gβγt (2 µM) were reconstituted to form heterotrimer (Gi) in 100 µl running buffer (25 mM Hepes, pH 7.4, 100 mM NaCl) overnight on ice. 80 µl of reconstituted Gi was injected to superdex 200 packed in a Tricorn 10/200 column (GE Healthcare) equilibrated with the running buffer. The elution profile was monitored by protein-intrinsic fluorescence with λex: 280 nm and λem: 340 nm at a flow rate of 1 ml/min. The retention time of the reconstituted Gi was integrated with UNICORN 5.2 software (GE Healthcare).

The invention claimed is:

1. A mutant human G protein alpha-subunit -$G\alpha_{i1}$-, wherein:
   (A) at least one amino acid residue of wild-type of the human G-protein-alpha-subunit-$G\alpha_{i1}$-, has been replaced;
   (B) the at least one amino acid residue replaced is selected from (1) a first group consisting of the amino acid residues with position R32A, K51A, K54A, I55A, I56A, H57A, R176A, E245A, T327A, N331A, V332A, and D350A (2) a second group consisting of amino acid residues with position G42A, A59G, T177A, D200A, A226G, E297A, A300G, and F334A, or (3) a third group consisting of amino acid residues with position V50A, R178A, and K180A; and
   (C) the wild-type of the human G protein alpha-subunit -$G\alpha_{i1}$- comprises residues 23–380 of SEQ ID NO:1:
   MGCTLSAEDKAAVERSKMIDRNLREDGE-
   KAAREVKLLLLGAGESGKSTIVKQMKIIHEAGY-
   SEE ECKQYKAVVYSNTIQSIIAII-
   RAMGRLKIDFGDSARADDARQL
   VLAGAAEEGFMTAELAGVI
   KRLWKDSGVQACFNRSREYQLND-
   SAAYYLNDLDRIAQPNYIPTQQDVLRTRVKTT-
   GIVETHFTF KDLHFKMFDVGGQRSERKKWIH
   CFEGVTAIIFCVALSDYDLVLAEDEEMNRM-
   HESMKLF DSICNNKWFTDTSIILFLNKKDL-
   FEEKIKKKEIYTHFTCATDTKNVQFVFDAVTD-
   VIIKNCGLF.

2. A mutant $G\alpha$ protein comprising a mutant human G protein alpha-subunit -$G\alpha_{a1}$-, wherein:
   (A at least one amino acid residue of wild-type human G protein alpha-subunit-$G\alpha_{i1}$- has been replaced with
   (B) the at least one amino acid residue replaced is selected from (1) a first group consisting of R32G.HNS1.3, K51G.H1.6, K54G.H1.9, I55G.H1.10, I56G.H1.11, H57G.H1.12, R176H.HF.6, E245G.H3.4, T327G.S6H5.4, N331G.H5.3, V332G.H5.4, and D350G.H5.22 (2) a second group consisting of G42G.S1H1.3, A59G.H1HA.2, T177G.HFS2.1, D200G.S3.7, A226G.S4.7, E297G.H4.2, A300G.H4.5, and F334G.H5.6, (3) a third group consisting of V50G.H1.5, R178G.HFS2.2, and K180G.HFS2.4, (C a common G protein numbering system (CGN) is used in the first, second, and third groups, wherein in said common G protein numbering system, the superscript next to the residue number denotes (i) either the GTPase (G) or helical (H) domain, (ii) the secondary structure element within each domain, and (iii) its position within this structural element according to a sequence alignment of 973 G protein sequences And (D) (the wild-type of the human G protein alpha-subunit -G$\alpha_{i1}$- comprises residues 23-380 of SEQ ID NO:1: MGCTLSAEDKAAVERSKMIDRNLREDGE-KAAREVKLLLLGAGESGKSTIVKQMKIIHEAGY-SEE ECKQYKAVVYSNTIQSIIAII-RAMGRLKIDFGDSARADDARQL VLAGAAEEGFMTAELAGVI KRLWKDSGVQACFNRSREYQLND-SAAYYLNDLDRIAQPNYIPTQQDVLRTRVKTT-GIVETHFTF KDLHFKMFDVGGQRSERKKWIHC FEGVTAIIFCVALSDYDLVLAEDEEMNRM-HESMKLF DSICNNKWFTDTSIILFLNKKDL-FEEKIKKKEIYTHFTCATDTKNVQFVFDAVTD-VIIKNCGLF.

* * * * *

SEQUENCE LISTING

```
<160> NUMBER OF SEQ ID NOS: 1

<210> SEQ ID NO 1
<211> LENGTH: 376
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Met Lys Lys His His His His His His His His His Glu Asn Leu
1               5                   10                  15

Tyr Phe Gln Gly Gly Ser Met Gly Cys Thr Leu Ser Ala Glu Asp Lys
                20                  25                  30

Ala Ala Val Glu Arg Ser Lys Met Ile Asp Arg Asn Leu Arg Glu Asp
            35                  40                  45

Gly Glu Lys Ala Ala Arg Glu Val Lys Leu Leu Leu Leu Gly Ala Gly
        50                  55                  60

Glu Ser Gly Lys Ser Thr Ile Val Lys Gln Met Lys Ile Ile His Glu
65                  70                  75                  80

Ala Gly Tyr Ser Glu Glu Glu Cys Lys Gln Tyr Lys Ala Val Val Tyr
                85                  90                  95
```

```
Ser Asn Thr Ile Gln Ser Ile Ile Ala Ile Ile Arg Ala Met Gly Arg
            100             105             110

Leu Lys Ile Asp Phe Gly Asp Ser Ala Arg Ala Asp Ala Arg Gln
        115             120             125

Leu Phe Val Leu Ala Gly Ala Ala Glu Glu Gly Phe Met Thr Ala Glu
    130             135             140

Leu Ala Gly Val Ile Lys Arg Leu Trp Lys Asp Ser Gly Val Gln Ala
145             150             155             160

Cys Phe Asn Arg Ser Arg Glu Tyr Gln Leu Asn Asp Ser Ala Ala Tyr
                165             170             175

Tyr Leu Asn Asp Leu Asp Arg Ile Ala Gln Pro Asn Tyr Ile Pro Thr
            180             185             190

Gln Gln Asp Val Leu Arg Thr Arg Val Lys Thr Thr Gly Ile Val Glu
        195             200             205

Thr His Phe Thr Phe Lys Asp Leu His Phe Lys Met Phe Asp Val Gly
    210             215             220

Gly Gln Arg Ser Glu Arg Lys Lys Trp Ile His Cys Phe Glu Gly Val
225             230             235             240

Thr Ala Ile Ile Phe Cys Val Ala Leu Ser Asp Tyr Asp Leu Val Leu
                245             250             255

Ala Glu Asp Glu Glu Met Asn Arg Met His Glu Ser Met Lys Leu Phe
            260             265             270

Asp Ser Ile Cys Asn Asn Lys Trp Phe Thr Asp Thr Ser Ile Ile Leu
        275             280             285

Phe Leu Asn Lys Lys Asp Leu Phe Glu Glu Lys Ile Lys Lys Ser Pro
    290             295             300

Leu Thr Ile Cys Tyr Pro Glu Tyr Ala Gly Ser Asn Thr Tyr Glu Glu
305             310             315             320

Ala Ala Ala Tyr Ile Gln Cys Gln Phe Glu Asp Leu Asn Lys Arg Lys
                325             330             335

Asp Thr Lys Glu Ile Tyr Thr His Phe Thr Cys Ala Thr Asp Thr Lys
            340             345             350

Asn Val Gln Phe Val Phe Asp Ala Val Thr Asp Val Ile Ile Lys Asn
        355             360             365

Asn Leu Lys Asp Cys Gly Leu Phe
    370             375
```